(12) United States Patent
Lachman et al.

(10) Patent No.: US 10,458,977 B2
(45) Date of Patent: Oct. 29, 2019

(54) SKIN TOPOGRAPHY AS A MARKER FOR SKIN MATURATION

(71) Applicant: Laboratoires Expanscience, Courbevoie (FR)

(72) Inventors: Nadege Lachman, Leymen (FR); Philippe Msika, Versailles (FR); Joachim Fluhr, Berlin (DE)

(73) Assignee: LABORATOIRES EXPANSCIENCE, Paris la Defense (FR)

( * ) Notice: Subject to any disclaimer, the term of this patent is extended or adjusted under 35 U.S.C. 154(b) by 419 days.

(21) Appl. No.: 15/310,303

(22) PCT Filed: May 15, 2015

(86) PCT No.: PCT/EP2015/060796
§ 371 (c)(1),
(2) Date: Nov. 10, 2016

(87) PCT Pub. No.: WO2015/173413
PCT Pub. Date: Nov. 19, 2015

(65) Prior Publication Data
US 2017/0241985 A1    Aug. 24, 2017

(30) Foreign Application Priority Data
May 15, 2014    (EP) .................... 14305714

(51) Int. Cl.
*G01N 33/50* (2006.01)
*A61B 5/00* (2006.01)
*G06T 7/00* (2017.01)

(52) U.S. Cl.
CPC ......... *G01N 33/5026* (2013.01); *A61B 5/442* (2013.01); *A61B 5/4848* (2013.01); *G01N 33/5044* (2013.01); *G06T 7/0012* (2013.01)

(58) Field of Classification Search
CPC ............ G01N 33/5026; G01N 33/5044; A61B 5/442; A61B 5/4848
See application file for complete search history.

(56) References Cited

U.S. PATENT DOCUMENTS

| | | | |
|---|---|---|---|
| 5,353,790 A * | 10/1994 | Jacques | G01N 21/4738 250/574 |
| 2005/0053637 A1 | 3/2005 | Ma'Or et al. | |
| 2015/0285787 A1 * | 10/2015 | Msika | G01N 33/5044 506/2 |

(Continued)

OTHER PUBLICATIONS

Haedersdal M, Efsen J, Gniadecka M, Fogh H, Keiding J, Wulf HC. "Changes in Skin Redness, Pigmentation, Echostructure, Thickness, and Surface Contour After 1 Pulsed Dye Laser Treatment of Port-wine Stains in Children". Arch Dermatol. 1998;134(2): 175-181. doi:10.1001/archderm.134.2.175 (Year: 1998).*

(Continued)

*Primary Examiner* — Utpal D Shah
(74) *Attorney, Agent, or Firm* — Potomac Law Group, PLLC (57) ABSTRACT

The present invention relates to a method for determining the relief of the skin surface of a subject, and hence the degree of maturation of the said skin surface. Methods for identifying active agents, raw materials and formulation are also provided.

26 Claims, 6 Drawing Sheets

Base Surface = Length x Width ≤ Relief Surface

Developed Surface = $\dfrac{\text{Relief Surface}}{\text{Base Surface}}$

(56) References Cited

U.S. PATENT DOCUMENTS

2017/0241985 A1* 8/2017 Lachman .............. A61B 5/442

OTHER PUBLICATIONS

Corcuff et al., "Skin relief and aging," Journal of the Society of Cosmetic Chemists, vol. 34, Jul. 1983, pp. 177-190.

Friedman et al., "3D In-Vivo Optical Skin Imaging for Topographical Quantitative Assessment of Non-Ablative Laser Technology", American Society for Dermatologic Surgery, vol. 28, 2002, pp. 199-204.

Latreille et al., "Recherché De Valeurs De Reference Du Micro-Relief Cutane En Fonction De L'Age Des Sujets", Journees de Statistiques, 2004, 6 pages (with English abstract).

Leveque, J.L., "EEMCO guidance for the assessment of skin topography," Journal of the European Academy of Dermatology and Venereology, vol. 12, 1999, pp. 103-114.

Mosteller, New England Journal of Medicine, vol. 317, No. 17, 1987, p. 1098.

Potorac et al., "In vivo skin relief measurement using a new optical profilometer," Skin Research and Technology, vol. 2, 1996, pp. 64-69.

Rhyu et al., "Scanning Electron Microscopic Observation of Human Skin Replica," Korean Journal of Microscopy, vol. 40, No. 4, 2010, pp. 267-270.

Rodrigues, Luis, "EEMCO Guidance to the in vivo Assessment of Tensile Functional Properties of the Skin," Skin Pharmacology and Applied Skin Physiology, vol. 14, 2001, pp. 52-67.

Tchvialeva et al., in "Skin Roughness Assessment, New Developments in Biomedical Engineering", Domenico Campolo (Ed.) ISBN: 978-953-7619-57-2, InTech, 2010, pp. 341-358.

Verbraecken et al., "Body surface area in normal-weight, overweigh, and obese adults. A comparison study," Metabolism Clinical and Experimental, vol. 55, 2006, pp. 515-524.

Zahouani et al., in "Measuring the Skin," P. Agache & P. Humbert Eds, Springer, 2004.

\* cited by examiner

Figure 1:

$Base\ Surface = Length \times Width \leq Relief\ Surface$ $Developed\ Surface = \dfrac{Relief\ Surface}{Base\ Surface}$

SKIN TOPOGRAPHY AS A MARKER FOR SKIN MATURATION

The skin is the largest organ of the human body and it has several functions. The most important is to protect the body against external influences.

The skin is a complex and multifunctional organ that consists of three main layers: the epidermis, the dermis and the subcutaneous connective tissue (also known as hypodermis or hypoderm).

The epidermis, which main role is the protection of the body, constitutes the most superficial layer of the body and ensures the impermeability of the skin and the resistance thereof. The epidermis is joined to the dermis by a zone rich in extracellular matrix and growth factors, called the dermo-epidermal junction, which ensures that the dermis adheres to the epidermis and thus maintains the dermo-epidermal cohesion. This structure has a mechanical support role which is partly responsible for the skin tonicity. The dermis is the skin layer between the epidermis and subcutaneous tissues. The dermis is primarily made up of connective tissue, such as collagen and elastin, which give the skin its elasticity and toughness. It thus cushions the body from stress and strain. Finally, the hypodermis is the innermost and thickest layer of the skin. It invaginates into the dermis and is attached to the latter, immediately above it, by collagen and elastin fibers. As it is essentially composed of adipocytes, cells specialized in accumulating and storing fats, it primarily acts as an energy reserve.

The skin surface is not flat. It is characterized by a special relief which probably reproduces the three dimensional organization of the deeper layers. This skin relief structure expresses the physical state of the integument, the organizational, mechanical, and sensorial properties thereof, and its possible alteration by physical factors or aging.

In particular, the organization of the skin, as well as its biomechanical and sensorial properties, is directly reflected by the topography of the skin surface. They are of great importance as they contribute to or are responsible for skin health and disease, structural integrity, cosmesis, and aging. They depend primarily on the nature and organization of the dermal collagen and elastic fibers network, which extend into the dermo-epidermal junction and the hypodermis, with less contribution by epidermis and stratum corneum. The dermis provides tensile strength and elasticity to the skin through an extracellular matrix composed of collagen fibers, microfibrers, and elastic fibers, embedded in proteoglycans. The collagen fibers (type I and type III) are responsible for mechanical properties of skin, while the elastic fibers give elasticity and suppleness to the skin. Thus the organization of the dermis layer, as well as of the dermo-epidermal junction and of the hypodermis, which is reflected by the relief of the skin surface, determines the mechanical and sensorial properties of the skin and its resistance to environmental aggressions.

Over the last decade, knowledge on newborn skin physiology has evolved. It is now clear that postnatal life is a time period of active functional maturation and cutaneous adaptation to the dry extra-uterine environment. Different environmental factors (for instance, dry and cold climate, diapers and cosmetic care procedures) influence the postnatal development of skin functional parameters. The evolution and maturation of the skin, most especially the dermis layer, but also of the dermo-epidermal junction and of the hypodermis, in turn enable resistance to such environmental factors. However, until the maturation of the skin is completed, a child remains highly sensitive to environmental aggressions, such as e.g. UV rays.

The evolution and maturation of the skin, and most specifically of the dermis layer (and additionally of the dermo-epidermal junction and of the hypodermis), is thus an important consideration in a number of cosmetic and clinical implications for children. For example, knowledge of the evolution/maturation stage of a subject's skin can help to quantify effectiveness (prevention and treatment) of cosmetic products such as creams or lotions, and to adapt these products to this specific child in relation to the maturation stage of his/her skin. In addition, changes in the evolution and maturation of the skin due to skin diseases in children may play a role in a better understanding and treatment of these diseases.

Prior studies have evaluated the maturation of the dermis, as well as of the dermo-epidermal junction and of the hypodermis, through the determination of its organization, as well as of its mechanical and sensorial properties. In particular, a number of methods have thus been used for measuring skin mechanical properties, e.g. tensile tests, torsion tests, suction methods, or indentation methods (Rodrigues, *Skin Pharmacol Appl Skin Physiol*, 14: 52-67, 2001). However, these methods have been applied primarily to the study of skin aging, but have never been used in children. In fact, all of them imply the use of a force (e.g. torsion) upon the skin in order to be capable of determining a specific mechanical property (e.g. elasticity). It is clear that this cannot be applied to children, especially younger ones, if only for ethical reasons. In addition, the results obtained through these methods can be highly dependent upon the conditions of the test, which make the interpretation of these results very complex. Finally, the sensitivity of these methods is quite low, and it is highly doubtful that these methods would enable discriminating between the skin of two children of different ages.

There is thus still a need for the development of new tools for assessing the maturation level of the skin in children.

DESCRIPTION

The present inventors have shown that the level of maturation of the skin, and thus of its organization, of its mechanical properties, and of it sensorial features, can easily be determined by evaluating the topography of the skin. In this respect, the inventors have developed a new, quantitative method which enables to reliably and reproducibly assess the maturation of the skin topography in children.

As used herein, the "evolution of the skin" means the processes through which the structure and the organization of the layers of the skin changes from birth to death. By "maturation of the skin", it is herein referred to the evolution of the skin in children. Without being bound by theory, it is thought that the maturation of the skin is associated with the construction of an organized and dense network of collagen and elastin fibers.

In order to elucidate the main cutaneous physiological functions in infants, one clinical study was performed. This study aimed at investigating non-invasively skin maturation, by characterizing infant skin in comparison to different children age groups and adult's skin.

The present invention thus relates to a method for determining the degree of maturation of the skin of a subject. In particular, the present inventors have observed that the degree of maturation of the skin is closely correlated with the development of the relief of the said skin.

The barrier organization/function of the skin is associated with the isotropy/anisotropy of the skin surface (unpublished data). In contrast, the degree of maturation of the skin surface reflects the organization of deeper layers of the skin, i.e. mostly the dermis, with a contribution from the dermo-epidermal junction and the hypodermis.

The method of the invention thus enables the characterization of the skin from birth and the monitoring of its evolution and maturation over time. A "child" means according to the invention an individual whose age is less than 16 years. In particular, are included within the category of children according to the invention, neonates of 1 to 15 days, infants of 5/6 weeks, infants of 6 months±1 month, infants of 1 year, and infants of 4 to 5 years, 7 years and 10 years. To avoid ambiguity, the term "child" used in this application without further explanation must be understood in its broadest sense, that is to say, as referring to a person under 16 years. An "adult" within the meaning of the present invention is a person who is not a child, i.e. a person aged over 16 years.

Preferably, the method of the invention can be used regardless of ethnicity or geographical skin, or phototype of it. It may well be of Caucasian, African, Asian, South American, Melanesian or any other origin; it can present a phototype I, II, III, IV, V or VI, without thereby affecting the invention. The method of the invention is indeed directed to the determination of skin maturation, regardless of the skin type, but depending only on donor age.

The present invention thus relates to a method for determining the degree of maturation of the skin of a subject, said method comprising a step of assessing the relief of the said skin.

By "relief" or "topography" of the skin surface, it is herein understood the elevations and depressions departing from the horizontal plane of the skin. The skin surface relief, or skin surface topography, combines schematically two types of relief, i.e. the microrelief and the macrorelief.

The "microrelief", as referred to herein, corresponds to the very fine lines network corresponds to the very fine lines network limiting geometrical shapes and which mainly results from the three-dimensional organization of the fibers (present in the superficial dermis) and the dermo-epidermal junction. The microrelief is mainly affected by the aging or/and the photoaging processes.

The "macrorelief" according to the invention includes deeper wrinkles and furrows. It is influenced not only by aging and photoaging processes but also by all mechanical stress induced by movement of muscles, bones, joints and expressions and mimics on the face.

The method of the invention thus comprises a step of assessing the microrelief or the macrorelief of the skin. Preferably, the method of the invention comprises a step of assessing the microrelief of the skin.

Skin is a highly non-linear, anisotropic, viscoelastic and nearly incompressible material. Its properties vary with age, from site to site and per person. This leads to difficulties in obtaining quantitative descriptions of mechanical properties of the skin. A second problem is the large variety of instruments, units and measurement conditions that was used which makes it hard to compare results.

Various methods have been developed to analyze the skin surface topography (Levêque, *J Eur Acad Dermatol Venereol*, 12: 103-114, 1999; Tchvialeva et al., in "Skin Roughness Assessment, New Developments in Biomedical Engineering", Domenico Campolo (Ed.), ISBN: 978-953-7619-57-2, InTech, 2010). However, these methods do not appear to be sensitive enough, whereas it is important to have a reliable method which can identify minimal variations and provide quantitative data in children.

The present inventors have found a new way of circumventing these problems. They have observed that the relief, and thus the degree of maturation of the skin, can be assessed by determining the developed surface of the said skin in children.

Human skin is not flat, but rather displays alternating plates and valleys. Hence the surface of the skin relief, including all the plates and valleys, is greater than the basic surface of the skin. The ratio between the elementary areas of the interfacial sides and the total surface which constitutes the analyzed area is "the developed skin surface" (Corcuff et al., *J. Soc. Cosmet. Chem.,* 34: 177-190, 1983; Zahouani and Vargiolu, in "Measuring the Skin", P. Agache & P. Humbert Eds, Springer, 2004; Latreille et al., XXXVI$^{èmes}$ Journées de Statistiques, 24-28 mai 2004, Montpellier, France). In other words, this parameter represents the ratio between the surface of the skin relief, taking into account all the elevations and depressions, and the basic surface of the skin.

It will be immediately be apparent to the person of skills in the art that the higher the developed surface, the more numerous and important the skin surface depressions and elevations are. The developed surface is thus a very good marker of the maturation of the skin for children.

Thus in a preferred embodiment, the present invention relates to a method of determining whether the skin of a child is mature or immature in its organization/function, said method comprising the steps of:
 a) taking a skin sample (A) of the said child; and
 b) determining the developed skin surface of the said skin sample.

In fact, the inventors have shown that the rate of increase of the developed skin surface is very high until 1 year, showing rapid maturation and reorganization of the skin. The period between 1 year and 4-5 years corresponds to a second phase of construction of the skin, slower, but also more complex. In other words, by the time a child reaches 4-5 years of age, the major part of the maturation and organization of his/her skin has been completed. After 4-5 years, the rate of increase is much slower and more regular than in the previous phase, indicating that the skin reaches progressively a mature organization. Thus, this period corresponds to a period of fine-tuning of the skin maturation and organization, where changes are incremental rather than dramatic.

On this basis, the inventors were able to distinguish three classes of skin surface maturation in relation to the age of the children:
 immaturity: 0 to 1 year;
 intermediate maturity: >1 years to 4-5 years; and
 maturity: >4-5 years.

The developed surface of the said skin sample can be compared to a reference obtained from the compilation of previous experimental results.

Alternatively, it is possible to compare the developed skin surface of the sample of the invention with the developed skin surface of a sample from a reference subject. By "reference subject", it is herein meant a subject whose age is known. Preferably, a reference subject is a newborn of 1 to 15 days, an infant of 5/6 weeks, an infant of 6 months±1 month, an infant of 1 year, an infant of 4 to 5 years, 7 years, 10 years or an adult of over 16 years.

A "skin sample" according to the invention comprises any sample reproducing the topography of the skin surface. Advantageously, the said skin sample is obtained from the surface of the skin by making a replica of the said skin surface. It is preferable to use replicas which are small enough to be laid flat on the child's skin. The person of skills in the art will be able to appreciate which replica to use depending on the child. Preferably, the said replica is a negative replica of the said skin surface. Such replicas have been widely used in the field and are thus well known to the person of skills in the art (Corcuff et al., *J. Soc. Cosmet. Chem.*, 34: 177-190, 1983; Levêque, *J Eur Acad Dermatol Venereol*, 12(2): 103-114, 1999; Friedman et al., *Dermatol Surg*, 28: 199-204, 2002; Zahouani and Vargiolu, in "Measuring the Skin", P. Agache & P. Humbert Eds, Springer, 2004; Latreille et al., XXXVI$^{èmes}$ Journées de Statistiques, 24-28 mai 2004, Montpellier, France; Rhyu et al., *Korean J. Microscopy*, 40(4): 267-270, 2010). Preferably, the said replica is made of silicon polymer. Various devices useful for this purpose are commercially available, such as, e.g. the Replica™—Repliflo Cartridge Kit (CuDerm) or the SIL-FLO kit (Monaderm).

Thus in a preferred embodiment, the present invention relates to a method of determining whether the skin of a child is mature or immature in its organization/function, said method comprising the steps of:
 a) taking a skin sample (A) of the said child, wherein the said skin sample is a replica of the skin surface; and
 b) determining the developed skin surface of the said skin sample.

The developed skin surface of the skin sample can be determined using any of the various methods of skin imaging known to the person of skills in the art. Advantageously, the said methods of skin imaging enable the person of skills in the art to observe and distinguish the topography of the skin. According to this embodiment, the said method enables the detection of the various planes and valleys constituting the relief of the skin.

For example, the skilled person can use any of the microscopy techniques commonly used in the laboratory. These techniques include, for example, methods of optical microscopy, such as conventional light microscopy, fluorescence microscopy, confocal/multiphoton microscopy and stimulated emission depletion; scanning probe microscopy, including scanning tunneling microscopy (STM), atomic force microscopy (AFM), near-field scanning optical microscopy and others; electronic microscopy; optical tomography, including optical coherence tomography; and optical profiling. Electronic microscopy techniques suitable for the method of the invention comprise such techniques as e.g. transmission electron microscopy (TEM), scanning transmission electron microscopy (STEM), focus ion beam microscopy (FIB) and scanning electron microscopy (SEM).

Preferably, the developed skin surface is determined using an optical profiler. An optical profiler is an interference microscope, and is used to measure height variations, such as surface roughness, on surfaces with great precision using the wavelength of light as the ruler. Optical interference profiling is a well-established method in the art of obtaining accurate surface measurements.

Optical profiling uses the wave properties of light to compare the optical path difference between a test surface and a reference surface. An optical profiler scans the material, i.e. the skin sample of the invention, vertically. As the material in the field of view passes through the focal plane, it creates interference. Each level of height in the said skin sample reaches optimal focus (and therefore greatest interference and contrast) at a different time. With well-calibrated optical profilers, accuracy well below a nanometer can be obtained.

Preferred optical profilers according to the invention include confocal microscopes and low coherence interferometers.

Optical profiling thus represents a very precise method for direct analysis of the topography of the skin sample. With its resolution it enables a high quality three-dimensional picture of skin topography and ultrastructure. More preferably, the developed surface of the said skin sample is determined by performing optical profiling. According to this embodiment, the developed skin surface is determined using the image of the skin sample obtained by optical profiling thus examined.

The said invention thus enables the person of skills in the art to determine whether a skin is mature or not, by taking a skin sample from a subject, said skin sample being a replica of the skin surface, performing optical profiling on the said skin sample, and determining the developed skin surface.

Thus, according to this embodiment, the present invention relates to a method of determining whether the skin surface of a child is mature or immature in its organization/function, said method comprising the steps of:
 a) taking a skin sample (A) of the said child, wherein the said skin sample is a replica of the skin surface;
 b) obtaining an image of the said skin sample by optical profiling, and c) determining the developed skin surface of the said sample.

In order to calculate the developed skin surface of the sample, it is not always possible to determine accurately the basic surface of the sample. Preferably, said basic surface is determined by the root mean square plane method, i.e. establishing the root mean square going through the experimental points. This method aims at minimizing the variations in relation to each of the coefficients of the average plane (Zahouani and Vargiolu, in "Measuring the Skin", P. Agache & P. Humbert Eds, Springer, 2004).

In order to determine which part of the developed skin surface genuinely represents the maturation of the skin, and not simply the general expansion of the skin as the infant grows, it may be advantageous to normalize the developed skin surface to the body surface area of the subject.

The body surface area is given by the Mosteller formula (Mosteller, *N Engl J Med*, 317(17): 1098, 1987):

$$BSA(m^2) = ([Height(cm) \times Weight(kg)]/3600)^{1/2}$$

More advantageously, the BSA of the subject is normalized to the average BSA in the adult population, resulting in a correction factor.

The value for the average BSA in the adult population can easily be found in the relevant publications, such as e.g. Verbraecken et al. (*Metabolism*, 55(4): 515-524, 2006).

The corrected developed skin surface is obtained by multiplying the developed skin surface by this correction factor.

Thus, according to this embodiment, the present invention relates to a method of determining whether the skin surface of a child is mature or immature in its organization/function, said method comprising the steps of:
 a) taking a skin sample (A) of the said child, wherein the said skin sample is a replica of the skin surface;
 b) obtaining an image of the said skin sample by optical profiling,
 c) determining the developed skin surface of the said sample,
 d) determining the body surface area (BSA) of the said child,
 e) determining the ratio between the BSA of the said child and the mean BSA value in the adult population, and f) determining the corrected developed skin surface of the said skin sample by multiplying the developed skin sample of step c) by the ratio of step e).

Functional and structural skin adaptation is a dynamic process which starts immediately after birth in humans, and which involves changes of the major properties of the skin as the skin matures, including modification of the organization of the skin, of its mechanical properties, and of it sensorial features. It would thus be desirable to use cosmetic products, i.e. active agents, cosmetic raw materials and/or cosmetic formulations, which are suited to the maturation level of the skin.

It will be clear to those skilled in the art that the invention has the advantage of enabling the easy isolation and characterization of active agents, cosmetic raw materials and/or cosmetic formulations. In particular, tolerance, skin penetration and efficiency of an active agent can easily be checked with the method of the invention.

More precisely, the present invention enables to verify that these agents are suited to the maturation stage of the skin of a specific class age. In particular, it is important to isolate agents which will reinforce or maintain the resistance organization/function of an immature or moderately mature skin surface, or to maintain the resistance organization/function of a mature skin. For example, it may be desirable to isolate agents which will greatly improve the maturation level of the skin in newborns, while agents respecting the skin surface maturation may be convenient for infants of 4-5 years.

In another aspect, the invention thus enables the isolation of active agents having an effect on the skin of children and, more particularly, to the skin of newborns of 1 to 15 days, infants of 5/6 weeks, infants of 6 months±1 month, infants of 1 year, and infants of 4 to 5 years, 7 years and 10 years. Specifically, the identification of the maturation stage of the skin according to the method of the invention enables the identification of active agents reinforcing or maintaining the resistance function of the said skin.

The invention therefore also relates to a method for identifying an active agent for the preparation of a dermo-cosmetic composition for child, said method comprising the steps of:
  a) obtaining at least one sample (A) of skin cells of a child;
  b) contacting a candidate active agent with the sample (A);
  c) determining the level of maturation of the skin of the sample (A) by the method of the invention;
  d) determining the level of maturation of the skin in a control sample;
  e) comparing the level of expression of step c) and the level of expression of step d), and
  f) determining whether said candidate active agent is an active agent for the preparation of a dermo-cosmetic composition of the skin of a child.

According to a preferred embodiment, the child from which the sample (A) is obtained is a newborn of 1 to 15 days, an infant of 5/6 weeks, an infant of 6 months±1 month, an infant of 1 year, or an infant of 4 to 5 years, 7 years and 10 years.

The control sample according to the invention is a sample that has not been in contact with the candidate active agent, thus allowing a significant comparison between the skin maturation level of step c) and that of step d). For example, the sample (A) that has not been contacted with the candidate can be used as a control. In this case, the maturation of the skin is evaluated in the sample (A) before and after being brought into contact with the candidate active agent.

The candidate is an active agent for preparing a cosmetic composition for the skin of a child, if said active agent maintains or improves the maturation level of the skin.

Preferably, the active agent of the invention is capable of restoring the normal level of skin maturation. By "normal level", it is herein referred to the level of maturation of the skin commonly observed in a population of healthy subjects of the same age as the subject. In other words, the treated skin displays a topography which is the same as the one observed in a population of healthy subjects of the same age. In other words, the developed surface is the same as the one observed in a population of healthy subjects of the same age.

Alternatively, the active agent of the invention is capable of leading to an improved level of skin maturation. By "improved level", it is herein referred to the level of maturation of the skin commonly observed in a population of healthy subjects of the same age as the subject. In other words, the topography of the treated skin is more developed than the one observed in a population of healthy subjects of the same age. In yet other words, the developed surface of the treated skin is superior to the one observed in a population of healthy subjects of the same age.

In another aspect, the invention enables the isolation of raw materials, which can be used in the development of formulations for the skin of the child and, more particularly, to the skin of newborns of 1 to 15 days, infants of 5/6 weeks, infants of 6 months±1 month, infants of 1 year, infants of 4 to 5 years, 7 years and 10 years. A formulation of the invention is a preparation obtained by mixing different raw materials, to meet a demand expressed generally in terms of properties. The formulations of the invention can be used in cosmetics, pharmaceutical, food and/or nutraceutical. They can be used in humans or animals, by oral or topical application.

The invention thus enables the identification of raw materials increasing tolerance and skin penetration. The determination of the skin maturation level according to the method of the invention allows the identification of raw materials or not modulating the said maturation.

The invention therefore also relates to a method for identifying a raw material that can be used for the preparation of a cosmetic, pharmaceutical, food and/or nutraceutical formulation for children, said method comprising the steps of:
  a) obtaining at least one skin sample (A) from a child;
  b) contacting a candidate raw material with the sample (A);
  c) determining the level of maturation of the skin of the sample (A) by the method of the invention;
  d) determining the level of maturation of the skin of a control sample;
  e) comparing the level of maturation of step c) and the level of maturation of step d), and
  f) determining if said material is a candidate material for the preparation of a cosmetic, pharmaceutical, food and/or nutraceutical formulation for children.

According to a preferred embodiment, the child from which the sample (A) is obtained is a newborn of 1 to 15 days, an infant of 5/6 weeks, an infant of 6 months±1 month, an infant of 1 year, or an infant of 4 to 5 years, 7 years or 10 years.

The control sample according to the invention is a sample that has not been in contact with the candidate raw material, thus allowing a significant comparison between the skin maturation level of step c) and that of step d). For example, the sample (A) that has not been contacted with the candidate raw material can be used as a control. In this case, the maturation of the skin is evaluated in the sample (A) before and after being brought into contact with the candidate raw material.

It is clear that the invention thus not only enables the isolation and characterization of raw materials that can be used in cosmetic, pharmaceutical, food and/or nutraceutical formulations, but also to test said formulations already made and to identify those that have optimal qualities of tolerance, efficacy, toxicology and skin penetration vis-à-vis a child's skin. Those skilled in the art will understand readily that that the identification of the maturation level of the skin according to the method of the invention is crucial in determining whether a formulation can be used on the skin of children.

The invention therefore also relates to a method for identifying a cosmetic, pharmaceutical, food and/or nutraceutical formulation for the skin of children, said method comprising the steps of:
  a) obtaining at least one sample (A) of skin cells of a child;
  b) contacting a candidate active formulation with the sample (A);
  c) determining the level of maturation of the skin of the sample (A) by the method of the invention;
  d) determining the level of maturation of the skin in a control sample;
  e) comparing the level of maturation of step c) and the level of maturation of step d), and
  f) determining whether said candidate formulation is a cosmetic, pharmaceutical, food and/or nutraceutical formulation for children.

According to a preferred embodiment, the child from which the sample (A) is obtained is a newborn of 1 to 15 days, an infant of 5/6 weeks, an infant of 6 months±1 month, an infant of 1 year, or an infant of 4 to 5 years, 7 years or 10 years.

The control sample according to the invention is a sample that has not been in contact with the candidate formulation, thus allowing a significant comparison between the skin maturation level of step c) and that of step d). For example, the sample (A) that has not been contacted with the candidate formulation can be used as a control. In this case, the maturation of the skin is evaluated in the sample (A) before and after being brought into contact with the candidate formulation.

According to another aspect of the invention, the level of maturation of the skin can be used to characterize skin disorders affecting children. Specifically, it is possible to characterize, using said maturation level of the invention, skin diseases affecting newborns, infants and/or children whose age is between 2 and 16.

By "skin disorder", it is herein referred to all abnormal reactions that can affect the skin of an individual. These conditions affect both the skin itself (that is to say, the epidermis, the dermo-epidermal junction, the dermis and/or the hypodermis), the pores of the skin, sweat and sebaceous glands attached thereto, hair or nails. Preferably, the skin disorders of the invention affect the deeper layers of the skin, that is the dermoepidermal junction, the dermis and/or the hypodermis.

Skin disorders according to the invention result in injuries, which correspond to a damaged skin or a skin in poor condition. Damaged skin includes such reactive sensitive skin, dry skin, skin damaged by the sun, by radiation, by the cold, by stress or pollution, by an allergy, urticaria, eczema and by other forms of dermatitis such as atopic dermatitis, impetigo, irritative dermatitis, particularly irritant dermatitis of the seat or diaper rash, contact dermatitis, seborrheic dermatitis of the skin and scalp (cradle cap), psoriasis, disease-Lainer Moussous, or through wounds or burns. Skin disorder is therefore meant to include disorders as diverse as herpes, angiomas (including tuberous, subcutaneous or plans), hemangiomas, baby acne, adolescent acne, ichthyoses (e.g. vulgaris, congenital, lamellaris . . . ) etc. A skin disorder can be caused or exacerbated by an external infection example of parasitic, viral, bacterial or fungal. The term "skin disorder" as used herein is also meant to encompass as well the warts, strophulus prurigo, scabies, head lice, or fungal infections. The latter are caused by parasitic fungi proliferation of parasites in the body. The most common fungal infections comprise candidiasis and pityrosporoses, which are caused by yeast overgrowth of the skin.

Such skin disorders can have potentially deleterious effects on the skin organizational, mechanical, and sensorial properties, including its capacity to resist to aggression, as is the case for, e.g., dry skin. Such effects could translate into an alteration of the maturation level of the skin.

According to this particular embodiment, the invention provides a method of determining if a skin disorder affects the maturation of the skin, said method comprising the following steps:
  a) obtaining at least one skin sample (A') of cells of a child affected by said skin disorder;
  b) obtaining at least one control sample (B) of skin cells of a healthy child;
  c) determining the level of maturation of the skin of the sample (A') by the method of the invention;
  d) determining the level of maturation of the skin of the sample of step b) by the method of the invention;
  e) comparing the level of maturation of step a) and the level of maturation of step b), and
  f) determining whether the level maturation of the skin is affected by the said skin disorder.

According to a preferred embodiment, the child from which the sample (A) is obtained is a newborn of 1 to 15 days, an infant of 5/6 weeks, an infant of 6 months±1 month, an infant of 1 year, or an infant of 4 to 5 years, 7 years or 10 years.

It will be immediately clear to the person of skills in the art that the effect of a skin disorder on the maturation of the skin is immediately advantageous for isolating agents active in treating the said disorder.

The invention therefore also relates to a method for identifying an active agent for treating a particular skin disorder in children, said method comprising the steps of:
  a) obtaining at least one skin sample (A') from a child affected by said skin disorder;
  b) contacting a candidate agent with the said sample (A');
  c) determining the level of maturation of the skin of the sample (A') by the method of the invention;
  d) determining the level of maturation of the skin of at least one control sample;
  e) comparing the level of maturation of step c) and the level of maturation of step d), and
  f) determining if said candidate is an active agent for treating skin disorders of children.

According to a preferred embodiment, the child from which the sample (A) is obtained is a newborn of 1 to 15 days, an infant of 5/6 weeks, an infant of 6 months±1 month, an infant of 1 year, or an infant of 4 to 5 years, 7 years or 10 years.

Preferably, the active agent of the invention is capable of restoring the normal level of skin maturation. By "normal level", it is herein referred to the level of maturation of the skin commonly observed in a population of healthy subjects of the same age as the patient affected by the said disorder. In other words, the relief of the treated skin is the same as the one observed in a population of healthy subjects of the same age. In still other words, the developed surface of the treated skin is the same as the one observed in a population of healthy subjects of the same age.

Alternatively, the active agent of the invention is capable of leading to an improved level of skin maturation. By "improved level", it is herein referred to the level of maturation of the skin commonly observed in a population of healthy subjects of the same age as the patient affected by the said disorder. In other words, the treated skin shows a relief more developed than the one observed in a population of healthy subjects of the same age. In yet other words, the developed surface of the treated skin is superior to the one observed in a population of healthy subjects of the same age.

The examples that follow are merely exemplary of the scope of this invention and content of this disclosure. One skilled in the art can devise and construct numerous modifications to the examples listed below without departing from the scope of this invention.

FIGURE LEGENDS

FIG. 4: A: Evolution of the corrected developed surface as a function of the age of the children (0-14 months); B: Evolution of the corrected developed surface as a function of the age of the children (12-60 months); C: Evolution of the corrected developed surface as a function of the age of the children (60-350 months). The points for each of the 3 identified maturation phases were used to draw a graph; the linear equation thereof was calculated using Excel.

EXPERIMENTAL EXAMPLE

In the study, replicas of the skin surface were collected on the volar forearm in 65 healthy male and female volunteers in 7 age groups (n=between 6 and 15 per group)
group 1: 5-6 weeks (n=9),
group 2: 6 months (±1 month; n=8),
group 3: 1 year (n=7),
group 4: 4-5 years (n=7),
group 5: 7 years (n=13),
group 6: 10 years (n=15)
group 7 (adults): 20-35 years old (; n=6).

The replicas were analyzed by confocal microscopy, as previously described (Zahouani and Vargiolu, in "Measuring the Skin", P. Agache & P. Humbert Eds, Springer, 2004).

A quantitative method of cutaneous relief imaging has been developed, wherein the topographical profile is considered as a distribution of heights spaced out at regular intervals (Zahouani and Vargiolu, in "Measuring the Skin", P. Agache & P. Humbert Eds, Springer, 2004). The said method thus makes use of quantitative parameters which enable monitoring the changes of the skin surface relief. In addition, both micro- and macroreliefs can be analyzed with this method at the same time.

Figure 1:
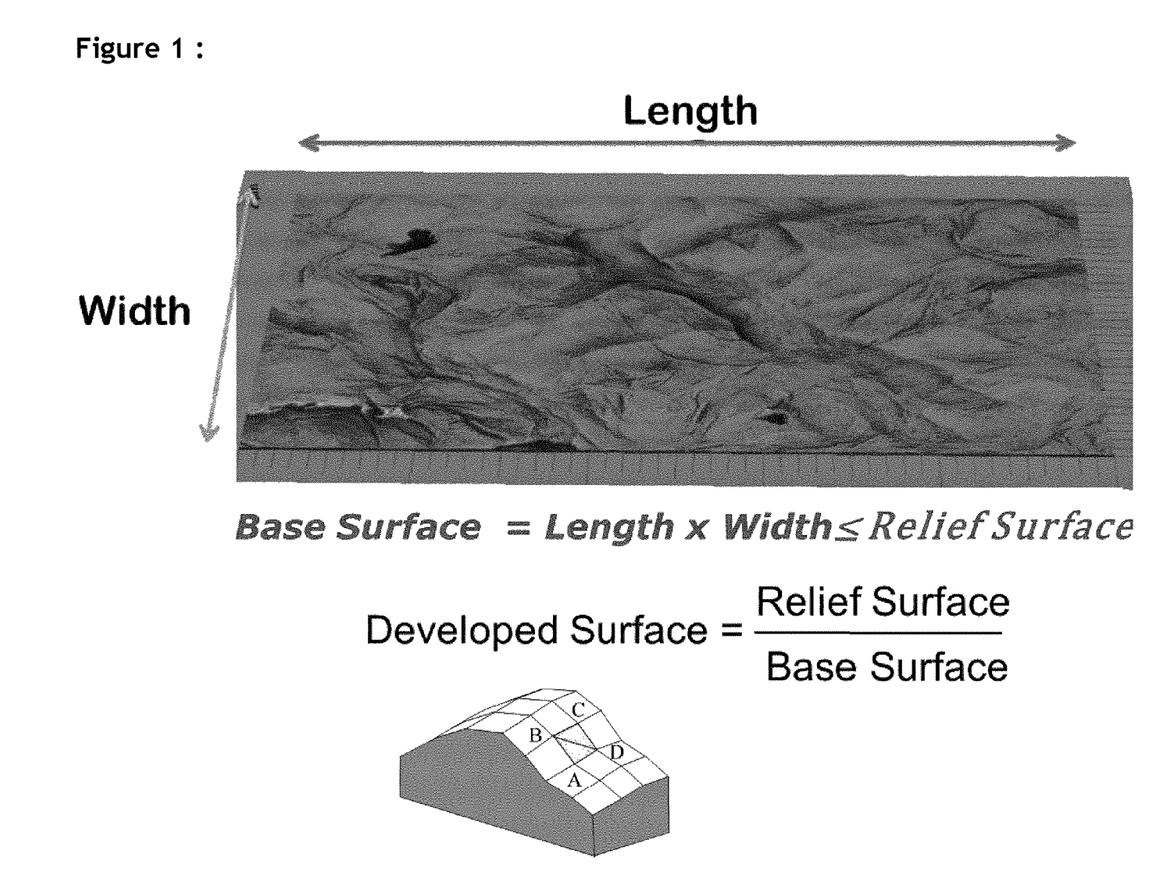
FIG. 1: Developed surface.

In particular, the said method enables the determination of the developed skin surface. The developed surface corresponds to the ratio between the area of the local elementary surfaces and the area of the measured zone (FIG. 1).

A first step according to this method is the identification of a reference plane of skin relief. Thus leveling the surface requires establishing the root mean square plane going through the experimental points. This method aims at minimizing the variations in relation to each of the coefficients of the average plane.

Then, the developed surface was calculated using the equation:

$$S_{Dev} = \frac{\sum_{j=1}^{N-1}\sum_{i=1}^{M-1} A_{ij}}{\text{Length} \times \text{Width}}$$

Figure 2:
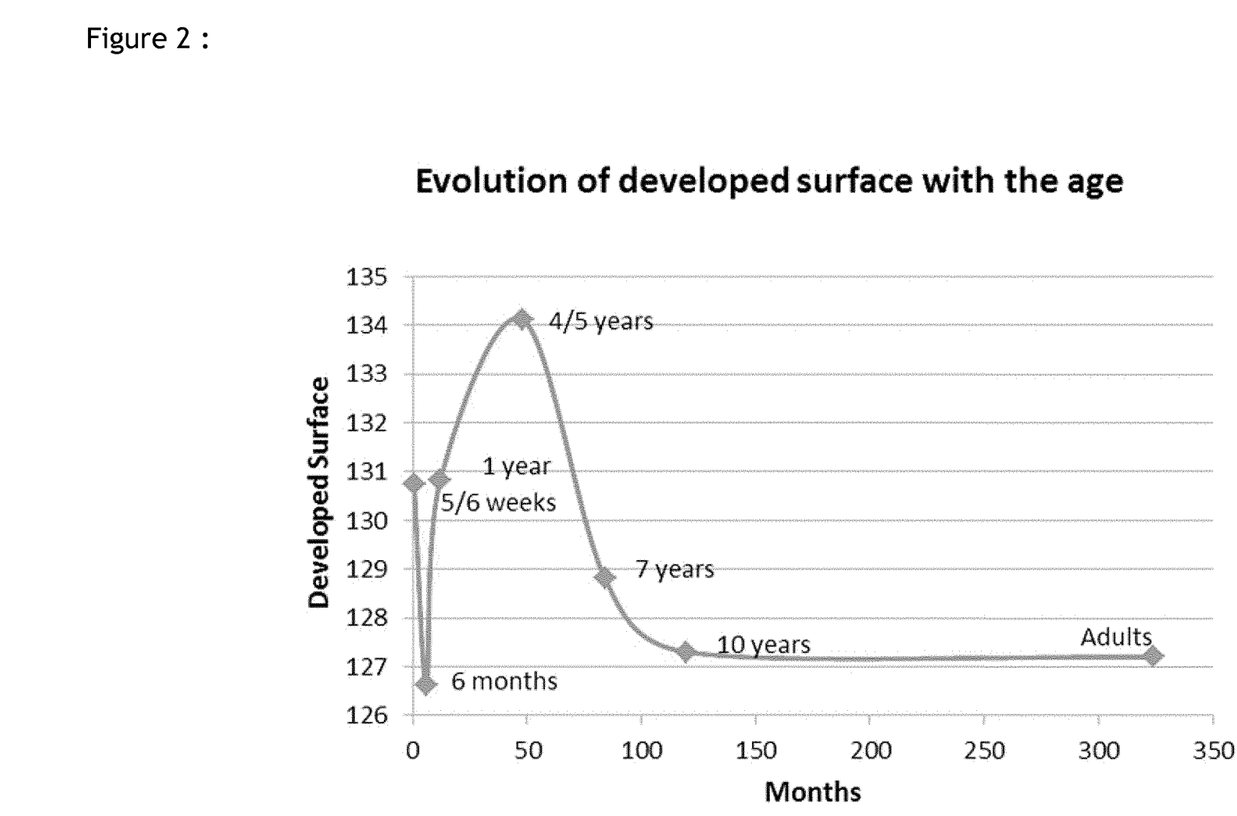
FIG. 2: Evolution of the developed surface as a function of the age of the children.

The resulting value showed a bell-shape distribution, with a peak at around 4-5 years (FIG. 2). This suggested a change in the maturation rate of the skin surface when children reached that age.

In order to confirm that this effect was not simply reflecting the general expansion of the skin surface, but was genuinely indicating an effect on the skin surface topography, the developed surface was linearized by a correction factor.

First, the body surface area in each age group was calculated according to the Mosteller formula (Mosteller, *N Engl J Med*, 317(17): 1098, 1987) using the mean height and weight of the said age group (Table 1):

$$BSA(m^2) = ([Height(cm) \times Weight(kg)]/3600)^{1/2}$$

TABLE 1

| Group | Enrolled subjects | Age (months) Mean | Weight (kg) Mean | Height (cm) Mean |
|---|---|---|---|---|
| 1 | 9 | 1.425 | 4.7 | 55.2 |
| 2 | 8 | 5.9 | 7.7 | 67.1 |
| 3 | 7 | 12 | 10.3 | 77.1 |
| 4 | 7 | 56.4 | 20.5 | 111.4 |
| 5 | 13 | 84 | 24.7 | 127.8 |
| 6 | 15 | 120 | 41.6 | 146.8 |
| 7 | 6 | 321.6 | 70.4 | 174.3 |

All the BSA values were then normalized to the BSA of the adults, giving a correction factor which in turn used to correct the developed surface values (Table 2). The corrected developed surface values thus genuinely reflect changes in the topography of the skin surface.

TABLE 2

| Age group | Developed surface | BSA | Correction factor | Corrected developed surface |
|---|---|---|---|---|
| 5/6 weeks | 130.7 | 0.27 | 0.15 | 19.05 |
| 6 months | 126.6 | 0.38 | 0.21 | 26.01 |
| 1 years | 130.8 | 0.47 | 0.25 | 33.28 |
| 4/5 years | 134.1 | 0.80 | 0.43 | 58.84 |
| 7 years | 128.8 | 0.94 | 0.51 | 65.35 |
| 10 years | 127.3 | 1.29 | 0.70 | 89.36 |
| adults | 127.28 | 1.84 | 1.00 | 127.28 |

Figure 3:
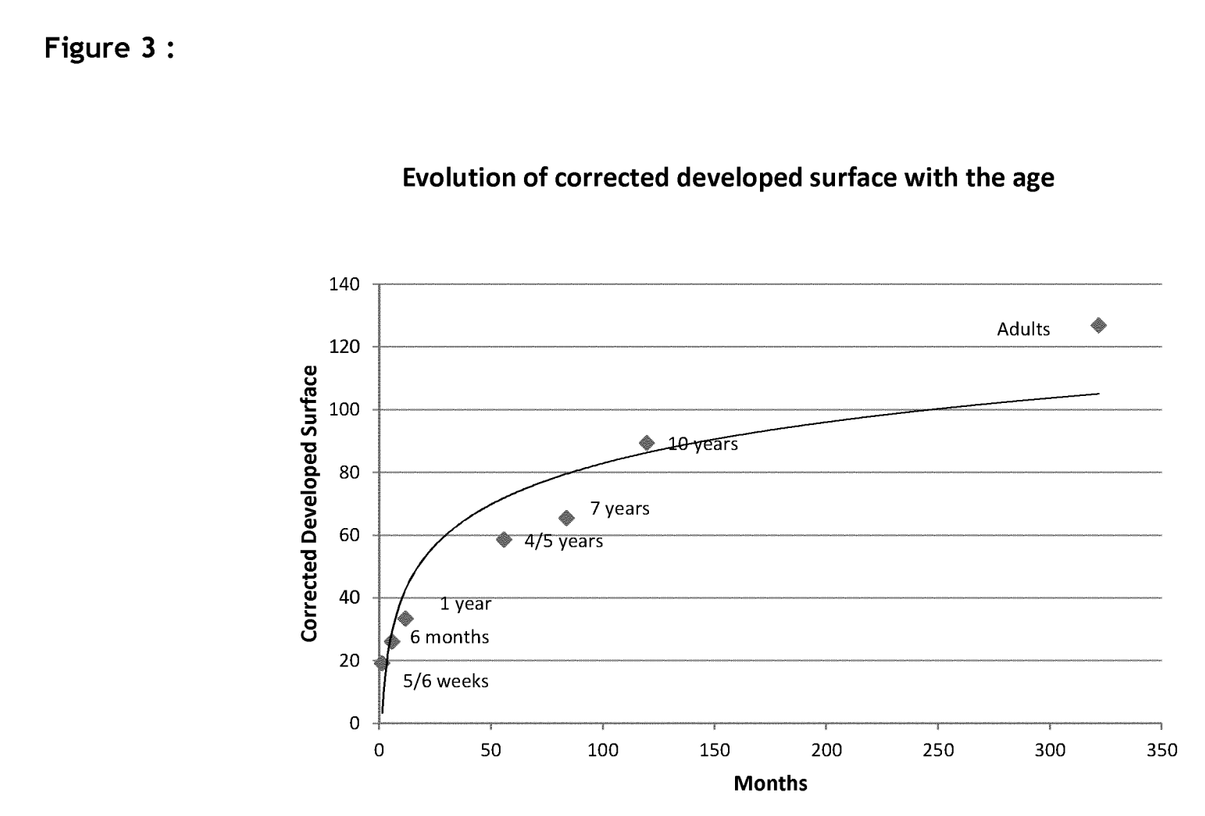
FIG. 3: Evolution of the corrected developed surface as a function of the age of the children.

FIG. 3 shows the increase in the corrected developed surface area as a function of age.

Figure 4:
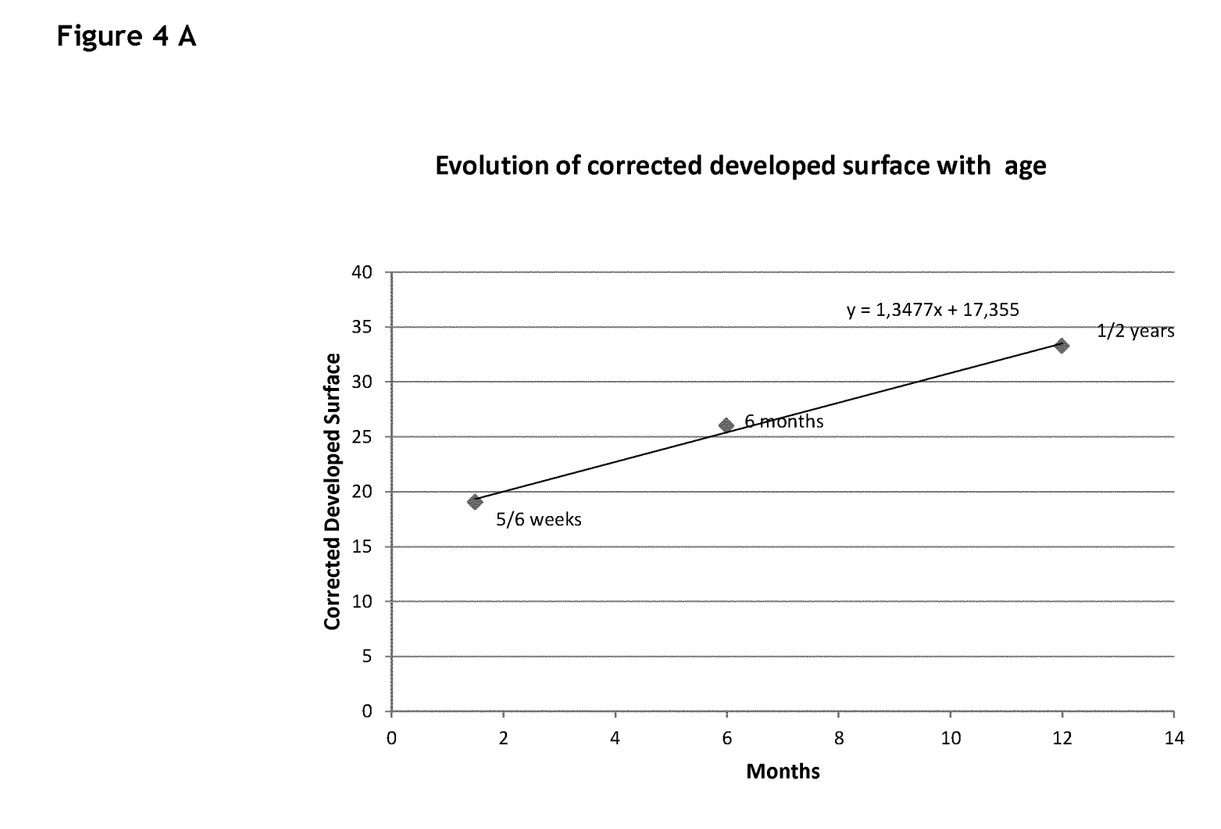

Three rates of development can clearly be observed. The developed surface grows very fast until 1 year, reflecting a strong maturation of the skin (rate=1.35). In infants between 1 year and 4-5 years, the rate decreases but is still strong, indicating a second phase of maturation which is slower but more complex than the first one (rate=0.57). Finally, after 4-5 years, the growth of the developed surface slows down (rate=0.25), confirming the inflexion point seen on FIG. 4.

In conclusion, the inventors have shown that the major part of the maturation of the relief of the skin is complete by the time the children reach 4-5 years. In the following years, the maturation of the skin continues, albeit at a slower rate, which likely corresponds to a period of fine-tuning of the skin organization.

The invention claimed is:
1. A method, comprising:
   a) obtaining at least one sample (A) of skin cells of a child;
   b) contacting a candidate cosmetic product with the sample (A);
   c) obtaining an image of the sample (A) after step b) using methods of optical microscopy, scanning probe microscopy, electronic microscopy, optical tomography or optical profiling;
   d) measuring the developed surface of the skin of the sample (A);
   e) obtaining at least one control sample of skin wherein said sample has not been in contact with the candidate cosmetic product of step b);
   f) obtaining an image of the control sample of step e) using methods of optical microscopy, scanning probe microscopy, electronic microscopy, optical tomography or optical profiling;
   g) measuring the developed surface of the skin of said control sample;
   h) preparing a dermo-cosmetic composition for the skin of a child comprising the candidate cosmetic product of step b) when the developed surface measured in step d) is superior or equal to the developed surface measured in step g).
2. The method of claim 1, further comprising the step of determining the body surface area (BSA) of the child of step a).
3. The method claim 2, further comprising the steps of determining the ratio between the BSA of said child and the average BSA value in the adult population, and determining the corrected developed surface of the skin sample (A) of step a) by multiplying the developed skin surface of step d) by said ratio.
4. The method of claim 1, wherein said skin sample (A) is a replica of the skin surface of the child of step a).
5. The method of claim 1, wherein:
   said methods of optical microscopy are selected from the group consisting of conventional light microscopy, fluorescence microscopy, confocal/multiphoton microscopy and stimulated emission depletion;
   said methods of scanning probe microscopy are selected from the group consisting of scanning tunneling microscopy (STM), atomic force microscopy (AFM), near-field scanning optical microscopy; and
   said method of optical tomography is optical coherence tomography.
6. The method of claim 1, wherein the image of step c) and the measurement of the developed skin surface of step d) for said sample (A) is obtained by using optical profiling.
7. The method of claim 6, wherein optical profiling includes confocal microscopy and low coherence interferometry.

8. The method of claim 1, wherein the child of step a) is a newborn of 1 to 15 days, an infant of 5/6 weeks, an infant of 6 months±1 month, an infant of 1 year an infant of 4 to 5 years, 7 years or 10 years.
9. The method of claim 1, further comprising the step i) of administering an effective amount of the dermo-cosmetic composition of step h) to the skin of the child of step a).
10. A method, comprising:
   a) obtaining at least one sample (A') of skin cells of a child affected by a skin disorder;
   b) obtaining an image of the sample (A') of step a) using methods of optical microscopy, scanning probe microscopy, electronic microscopy, optical tomography or optical profiling;
   c) measuring the developed surface of the skin of said sample (A');
   d) obtaining at least one control sample (B) of skin cells of a healthy child;
   e) obtaining an image of the sample (B) of step d) using methods of optical microscopy, scanning probe microscopy, electronic microscopy, optical tomography or optical profiling;
   f) measuring the developed surface of the skin of said sample (B);
   g) administering a composition or the formulation to the skin of the child of step a) for treating said skin disorder when the developed surface measured in step f) is superior or equal to the developed surface measured in step c).
11. The method of claim 10, further comprising the step of determining the body surface area (BSA) of the child of step a).
12. The method claim 11, further comprising the steps of determining the ratio between the BSA of said child and the average BSA value in the adult population, and determining the corrected developed surface of the skin sample (A') of step a) by multiplying the developed skin surface of step c) by said ratio.
13. The method of claim 10, wherein said skin sample (A') is a replica of the skin surface of the child of step a).
14. The method of claim 10, wherein:
   said methods of optical microscopy are selected from the group consisting of conventional light microscopy, fluorescence microscopy, confocal/multiphoton microscopy and stimulated emission depletion;
   said methods of scanning probe microscopy are selected from the group consisting of scanning tunneling microscopy (STM), atomic force microscopy (AFM), near-field scanning optical microscopy; and
   said method of optical tomography is optical coherence tomography.
15. The method of claim 10, wherein the image of step b) and the measurement of the developed skin surface of step c) for said sample (A') is obtained by using optical profiling.
16. The method of claim 15, wherein optical profiling includes confocal microscopy and low coherence interferometry.
17. The method of claim 10, wherein the child of step a) is a newborn of 1 to 15 days, an infant of 5/6 weeks, an infant of 6 months±1 month, an infant of 1 year an infant of 4 to 5 years, 7 years or 10 years.
18. A method, comprising:
   a) obtaining at least one sample (A') of skin cells of a child affected by a skin disorder;
   b) contacting a candidate active agent with the sample (A') of step a);

c) obtaining an image of the sample (A') of step b) using methods of optical microscopy, scanning probe microscopy, electronic microscopy, optical tomography or optical profiling;
d) measuring the developed surface of the skin of said sample (A');
e) obtaining at least one control sample of skin cells wherein said sample has not been in contact with the candidate active agent of step b);
f) obtaining an image of the control sample of step e) using methods of optical microscopy, scanning probe microscopy, electronic microscopy, optical tomography or optical profiling;
g) measuring the developed surface of the skin of said control sample;
h) preparing a pharmaceutical formulation for children comprising the candidate active agent of step b) when the developed surface measured in step d) is superior or equal to the developed surface measured in step g).

19. The method of claim 18, further comprising the step of determining the body surface area (BSA) of the child of step a).

20. The method claim 19, further comprising the steps of determining the ratio between the BSA of said child and the average BSA value in the adult population, and determining the corrected developed surface of the skin sample (A') of step a) by multiplying the developed skin surface of step d) by said ratio.

21. The method of claim 18, wherein said skin sample (A') is a replica of the skin surface of the child of step a).

22. The method of claim 18, wherein:
said methods of optical microscopy are selected from the group consisting of conventional light microscopy, fluorescence microscopy, confocal/multiphoton microscopy and stimulated emission depletion;
said methods of scanning probe microscopy are selected from the group consisting of scanning tunneling microscopy (STM), atomic force microscopy (AFM), near-field scanning optical microscopy; and
said method of optical tomography is optical coherence tomography.

23. The method of claim 18, wherein the image of step c) and the measurement of the developed skin surface of step d) for said sample (A') is obtained by using optical profiling.

24. The method of claim 23, wherein optical profiling includes confocal microscopy and low coherence interferometry.

25. The method of claim 18, wherein the child of step a) is a newborn of 1 to 15 days, an infant of 5/6 weeks, an infant of 6 months±1 month, an infant of 1 year an infant of 4 to 5 years, 7 years or 10 years.

26. The method of claim 18, further comprising the step i) of administering an effective amount of the pharmaceutical formulation of step h) to the skin of the child of step a).

* * * * *